United States Patent [19]

Roberts

[11] 4,370,134
[45] Jan. 25, 1983

[54] ONE PIECE PERMANENT SUPPORT FRAME FOR UPPER DENTURES

[76] Inventor: Harold D. Roberts, 1862 W. Broadway, Vancouver, B.C., Canada, V6J 1Y5

[21] Appl. No.: 212,608

[22] Filed: Dec. 3, 1980

[51] Int. Cl.³ .............................................. A61C 8/00
[52] U.S. Cl. .................................... 433/173; 433/172
[58] Field of Search ............... 433/173, 201, 176, 174, 433/175, 167, 171; 128/92 C; 3/1.9

[56] References Cited

U.S. PATENT DOCUMENTS

| | | | |
|---|---|---|---|
| 2,210,424 | 8/1940 | Morrison | 433/175 |
| 2,644,231 | 7/1953 | Brennan | 433/173 |
| 3,889,375 | 6/1975 | Roberts | 433/176 |
| 3,992,780 | 11/1976 | Herskovits | 433/176 |
| 4,145,764 | 3/1979 | Suzuki et al. | 433/176 |

*Primary Examiner*—Paul J. Hirsch
*Assistant Examiner*—John J. Wilson
*Attorney, Agent, or Firm*—Eugene M. Eckelman

[57] ABSTRACT

A frame has a pair of rails extending substantially in parallel relation. These rails are secured together at spaced points by cross webs and posts depend from these cross webs which support tooth-like portions secured together. The rails are arranged to be implanted respectively in grooves cut in the lower edge of the alveolar ridge of the upper jaw bone and in an area inwardly of the mouth of such edge such as in the palatine bone. The rails, posts and tooth-like portions are integrated into a one-piece unit and are all coated with porcelain to provide an attractive assembly as well as to provide structure that forms a physiological seal with mouth tissue.

3 Claims, 5 Drawing Figures

ONE PIECE PERMANENT SUPPORT FRAME FOR UPPER DENTURES

BACKGROUND OF THE INVENTION

This invention relates to a one-piece permanent support frame for upper dentures and more particularly is concerned with implants to be placed and permanently mounted in the upper jaw.

Upper jaw implants have heretofore been used for the purpose of providing permanently supported denture means. Some of such prior structures, such as shown in applicant's U.S. Pat. No. 3,889,375, contain a U-shaped body member arranged to be fitted in a groove cut in the alveolar ridge of the upper jaw for receiving an implant rail contoured as necessary. While the single rail structure provides adequate support for dentures in most instances even though there is deterioration or damage of the jaw bone, a single rail may not be adequate in conditions of serious bone deterioration and/or damage.

Also, in previous implants of the type described, the denture portions of the implant, as well as portions of the support members, contain joints or other connections which frequently are the source of low grade infections. In addition, support portions of implants, due to the material used and construction methods, do not form a good physiological seal with soft tissue of the mouth. Further yet, as the gums of patients recede due to aging, unsightly and unnatural looking support portions of some of the prior art dentures become exposed.

SUMMARY OF THE INVENTION

According to the present invention and forming a primary objective thereof, a one-piece permanent support frame for an upper denture is provided which has a double rail as the implant portion, such double rail construction being selectively constructed so that one of the rails is fitted in a groove in the alveolar ridge and the other rail is fitted in a groove cut in an area adjacent to the alveolar ridge such as in the palatine bone of the maxilla, thus providing a maximum support for implants in persons who have serious deterioration or damage to the alveolar ridge of the jaw bone.

Another object of the invention is to provide a novel structure of implant frame and integrated tooth structure which provides a good physiological seal with the tissue of the mouth and which also remains attractive even though there is substantial recession of the gums.

In carrying out the objectives of the invention, the support frame includes a pair of rails shaped similar to the contour of the alveolar ridge and secured together at spaced points by cross webs. The pair of rails are arranged to fit in grooves selectively cut in the alveolar ridge and in an area adjacent to the alveolar ridge such as in the palatine bone. Integrated denture means are supported on the frame by depending posts, and such denture means as well as all portions of the implant frame are coated with porcelain to provide a good physiological seal with tissue of the mouth as well as to provide an attractive appearance even though there is a substantial recession of the gums.

The invention will be better understood and additional objects and advantages will become apparent from the following description taken in connection with the accompanying drawings.

DETAILED DESCRIPTION OF A PREFERRED EMBODIMENT

Figure 4:
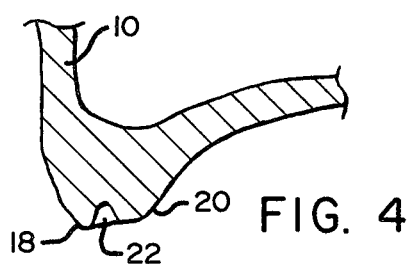
FIG. 4 is a fragmentary view taken similar to FIG. 2 but showing bone structure and a condition of serious deterioration of the alveolar ridge which may warrant installation of the present implant.
Figure 5:
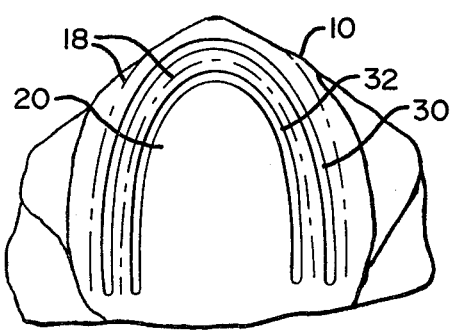
FIG. 5 is a fragmentary bottom plan view of an upper jaw bone.
Figure 3:
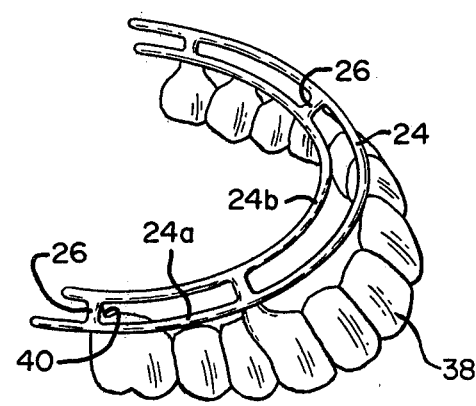
FIG. 3 is a perspective view of the denture support frame.

With particular reference to the drawings, reference is first made to FIGS. 1, 2, 4 and 5 which show an upper jaw portion 10 of a person 12, the numeral 14 designating the lower jaw having natural or artifical teeth 16. The numeral 18 designates the alveolar ridge of the upper jaw 10, the numeral 20 designates an inner area of the jaw known as the palatine bone, and the numeral 22 designates a tooth socket. With particular reference to FIG. 4, the alveolar ridge is shown in an exemplary badly deteriorated or damaged condition wherein a substantial amount of the lower portion of this ridge is missing, thus making it difficult to provide the patient with dentures or even to provide such patient with a single rail implant of the type illustrated in applicant's U.S. Pat. No. 3,889,375. The invention is concerned with an implant support frame which not only is arranged to be anchored in the alveolar ridge but also in an area adjacent to such ridge so as to take advantage of the strength provided by compact bone in such area such as in the palatine bone.

In carrying out the invention, the denture support frame 24 comprises two bar-like rails or struts 24a and 24b extending substantially in parallel relation with each other and connected together by integral cross webs 26 located at spaced points around the frame.

Figure 1:
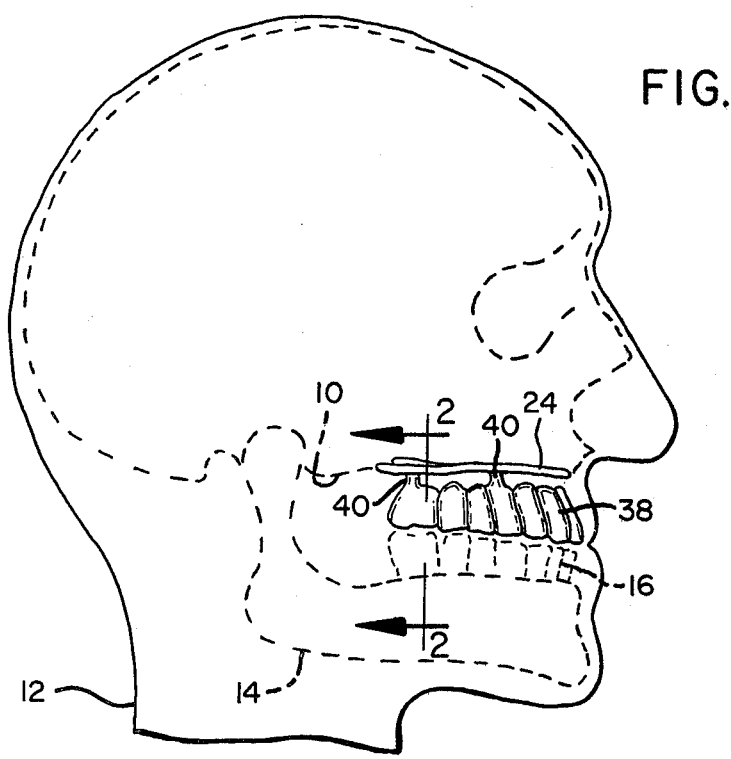
FIG. 1 is a side elevational view of a denture support frame of the invention as applied to the upper jaw of a person.
Figure 2:
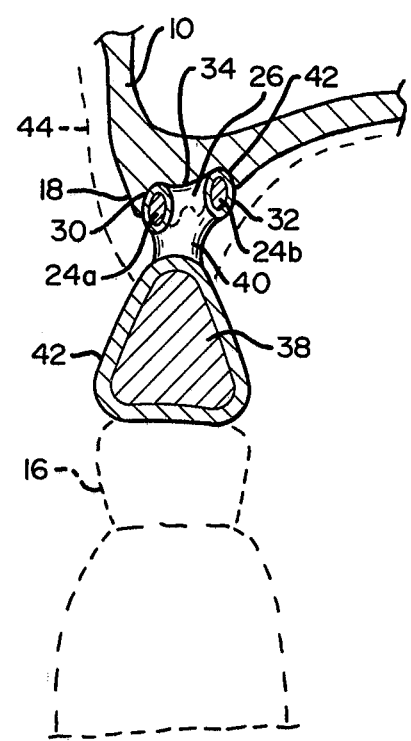
FIG. 2 is an enlarged fragmentary sectional view taken on the line 2—2 of FIG. 1.

The frame is shaped substantially to that of the longitudinal contour of the alveolar ridge 18 and is specifically constructed for implanting in the alveolar ridge and also in an adjacent area, such as in the palatine bone adjacent to the alveolar ridge. For the purpose of such installation, a groove 30, FIG. 2, is cut in the bottom edge of the alveolar ridge to the necessary depth for receiving the rail 24a. Also, a groove 32 is cut in an area adjacent to the alveolar ridge, such as in the palatine bone, for receiving the rail 24b. Cross grooves 34 may have to be cut to receive the webs 26.

The frame 24 is custom made for designated patients for proper location of the rail 24a in the most compact portion of the alveolar ridge and the best location of the rail 24b in an adjacent area. Rail 24b will generally be higher than the rail 24a since it usually will be embedded in the inwardly disposed area of the jaw bone.

Upon healing of the bone around the two rails as well as around the connecting webs 26, a good anchoring function is accomplished by the double rail structure. The bone disposed inwardly of the mouth from the aveolar ridge is baselar bone which as known is a compact type bone structure. Upon healing of the bone around the rail 24b a sturdy implant is provided to assist the hold of the less compact bone of the alveolar ridge on the rail 24a. The rails may or may not be entirely embedded in the grooves, each particular case depending upon the bone thickness of the particular patient and the deterioration of and/or damage to the jaw bone.

Another feature of the invention resides in the integrated structure of the artificial teeth 38 which depend from the frame 26. In such structure, the tooth-like portions 38 are properly shaped but comprise a one-piece unit. Such may be done by casting, welding, or other method of providing an integrated denture. Depending posts 40 are secured integrally between the cross webs 26 and the integrated tooth assembly 38. Since the posts are secured solidly to the frame 26 and also secured solidly to the tooth assembly 38, an over-all one-piece structure is provided.

The entire frame and tooth assembly preferably is provided with a porcelain coating 42 since it has been found that porcelain is compatible with mouth tissue 44 and furthermore provides a good physiological seal with such tissue. Since the implant and the teeth are all one piece, there are no joints to come loose. Furthermore since there are no joints, there are no places which may collect tartar, food, plaque or bacteria, and infection is thus kept to a minimum. Also, since the entire structure is coated with porcelain, there will be no material change in appearance of the tooth-like portions at the gum line when the gums recede due to aging of the patient. The denture will thus always be attractive.

Although the present illustration of the invention shows the rails 24a and 24b as extending the full length of the denture, it is to be understood that such rails may extend only part way, such as for example the implant frame may merely comprise double rail side portions. Such segmental arrangement is possible because of the integrated tooth assembly which is rigid and self-supporting, it merely being necessary to provide suitable connection between the implant frame and the teeth by the posts 40. As an example, the front portion of one or both rails may be omitted between the nearest cross webs 26, the posts together with the integrated tooth portions providing the necessary connection to the side implanted portions.

It is to be understood that the form of my invention herein shown and described is to be taken as a preferred example of the same and that various changes in the shape, size and arrangement of parts may be resorted to without departing from the spirit of my invention, or the scope of the subjoined claims.

Having thus described my invention, I claim:

1. A permanent implant denture support frame arranged for association with the upper jaw of a person, comprising
   (a) a frame portion consisting of first and second bar-like rails extending substantially in parallel relation,
   (b) said rails being spaced from each other in selected parallel relation so as to allow said first rail to fit in a groove cut along the alveolar ridge and said second rail to fit in another groove cut in the jaw bone inwardly of the mouth relative to the alveolar ridge,
   (c) cross webs securing said parallel rails together at spaced points throughout the length of said frame portion,
   (d) and artificial denture means depending integrally from said frame portion,
   (e) said frame being shaped similar to the contour of the upper jaw of a person so that said rails are arranged to fit in the respective grooves.

2. The denture support frame of claim 1 wherein said artificial denture means comprise teeth secured to each other in an integrated unit, and post means securing said integrated tooth assembly in depending relation from said frame portion.

3. The denture support frame of claim 1 wherein said second rail is disposed in an elevated plane relative to said first rail for fitting in the groove cut in the jaw bone inwardly of the mouth above the groove for the first rail, said cross webs angling upwardly therebetween to accommodate the higher positioning of said second rail.

* * * * *